United States Patent [19]

Grunewalder et al.

[11] Patent Number: 5,228,905

[45] Date of Patent: Jul. 20, 1993

[54] WATER-BORNE TREATMENT COMPOSITIONS FOR POROUS SUBSTRATES

[75] Inventors: John F. Grunewalder, Mequon, Wis.; Mark A. Voelker, Butler, Pa.

[73] Assignee: PPG Industries, Inc., Pittsburgh, Pa.

[21] Appl. No.: 795,410

[22] Filed: Nov. 20, 1991

Related U.S. Application Data

[63] Continuation-in-part of Ser. No. 567,036, Aug. 14, 1990, abandoned.

[51] Int. Cl.$^5$ ............................................. C09D 191/06
[52] U.S. Cl. ................................... 106/2; 106/271; 106/18.29; 524/490
[58] Field of Search .............. 106/2, 271, 18.29; 252/310; 524/490

[56] References Cited

U.S. PATENT DOCUMENTS

| | | | |
|---|---|---|---|
| 3,281,318 | 10/1966 | Stutz | 106/15 |
| 3,376,144 | 4/1968 | Stutz | 106/15 |
| 3,617,314 | 11/1971 | Hill | 106/2 |
| 4,323,602 | 4/1982 | Parker | 427/298 |
| 4,335,109 | 6/1982 | Hill | 424/140 |
| 4,360,385 | 11/1982 | Grunewalder | 106/2 |
| 4,404,239 | 9/1983 | Grunewalder | 584/490 |
| 4,533,254 | 8/1985 | Cook | 366/176 |
| 4,612,255 | 9/1986 | Hein | 428/541 |
| 4,783,502 | 11/1988 | Faler et al. | 524/871 |
| 5,037,653 | 8/1991 | Dawson | 424/405 |

FOREIGN PATENT DOCUMENTS

| | | |
|---|---|---|
| 1207952 | 7/1986 | Canada . |
| 040106 | 11/1981 | European Pat. Off. . |
| 2128091 | 4/1984 | United Kingdom . |

OTHER PUBLICATIONS

Chemical Engineers' Handbook, 5th Edition, Perry, pp. 21-6-8, 1973.

*Primary Examiner*—Mark L. Bell
*Assistant Examiner*—C. M. Bonner
*Attorney, Agent, or Firm*—Dennis G. Millman

[57] ABSTRACT

A treating composition for a porous substrate such as wood is provided in the form of an oil-in-water dispersion comprising a dispersed phase of an organic solvent in relatively low amounts to reduce V.O.C., a water repellent, and a stabilizing surfactant. Optionally, preservatives and resins may be included. Penetration with relatively low organic solvent content is achieved by producing a dispersion having a maximum mean particle size of 3000 Å. Also disclosed is a method of preparing the dispersion with a microfluidizer.

28 Claims, No Drawings

WATER-BORNE TREATMENT COMPOSITIONS FOR POROUS SUBSTRATES

RELATED APPLICATION

This application is a continuation-in-part of U.S. patent application Ser. No. 07/567,036 filed Aug. 14, 1990, now abandoned.

BACKGROUND OF THE INVENTION

The invention is directed to an aqueous treatment composition and a method for rendering porous substrates water repellent and for preserving porous substrates utilizing the aqueous treatment composition.

Generally, the art-known porous substrate treatment compositions such as wood treatment compositions are organic solvent-borne compositions. For example, U.S. Pat. Nos. 4,360,385 and 4,404,239 are directed to solvent-borne wood treatment compositions containing olefin and paraffin materials containing a substantial proportion of compounds containing from about 20 to 24 carbon atoms and, optionally, additives such as wood preservatives, alkyd resins and organic ionizable compounds. It is disclosed in the aforesaid United States patents that such art-known organic solvent-borne wood treatment compositions can provide wood with water-repellency at an efficiency level of at least about 40 percent, preferably at least about 50 percent and more preferably at least about 60 percent as determined by the N.W.M.A. Swellometer Test described in detail in a publication identified as NWMA-M-2-81, published by the National Woodwork Manufactures Association.

Increasing environmental concerns have generated an ever increasing need to develop treatment compositions with lower levels of organic solvents. One approach to reducing the organic solvent content investigated by the present inventors involves the utilization of an aqueous treatment composition. However, heretofore water-borne wood treatment compositions have not been able to provide nearly the level of water-repellency to wood as organic solvent-borne treatment compositions. For example, N.W.M.A. Swellometer Test NWMA-M-2-81, Sec. 3.2.1 concerning the method of treating wood for the purposes of the test discloses that the five test specimens (immersed) in the formulation to be tested have an immersion time for solvent-based formulations of 30 seconds and immersion time for water-borne formulations of 3 minutes. In part, the difficulty in water-repellency is believed to be due to the inefficient penetration of the wood by the water-borne formulation. Penetration of wood by water is inefficient because water, upon penetrating wood, swells the wood and hinders further penetration of the wood. Hence, other ingredients are hindered from penetrating the wood in a short exposure time. By the present invention, there is provided an aqueous wood-treating composition having penetration and water-repellency that is comparable to that of solvent-borne compositions.

U.S. Pat. No. 4,612,255 (Hein) discloses water dispersible wood treatment compositions. However, the compositions still include substantial amounts of organic solvent (the zinc-containing preservatives employed contain about 44% mineral spirits), such that the volatile organic content is greater than desired. In the examples set forth in that patent the V.O.C. ranges from 3.72 to 4.06. It would be desirable for the V.O.C. to be less than 3.5, preferably less than 3.0. It may also be noted that the water reducible concentrates in the Hein patent are totally organic compositions, not waterborne dispersions. Thus, Hein relies upon substantial amounts of surfactant to permit reduction with water, and high levels of surfactant can detrimentally affect penetration of treatment solutions into wood. It appears that penetrability of Hein's compositions rely upon the relatively large amounts of organic solvents that are included.

SUMMARY OF THE INVENTION

In accordance with the foregoing, the present invention encompasses an aqueous treatment composition for porous substrates in the form of a dispersion in water of a relatively small amount of substrate-penetrating solvent in amounts that limit V.O.C. to less than 3.5, preferably less than 3.0, relatively small amounts of surfactants, and water repellent compound capable of providing a wood substrate with water repellency at a level of at least 40 percent and up to 60 percent or higher as determined by NWMA-M-2-81 modified in that the immersion time for said aqueous wood-treatment composition for NWMA-M-2-81 is 30 seconds instead of 3 minutes.

The compositions of the present invention may be in the form of a water reducible concentrate or a diluted solution ready for application. The ready to use form of the invention may be characterized as an aqueous dispersion comprising (all percentages being on a weight basis): at least 1 percent but less than 10 percent (preferably less than 7.5 percent) of a porous substrate penetrating, organic solvent; at least 1 percent (preferably at least 1.5 percent) of a water repellent selected from the group consisting of an alpha-olefin or paraffin blend having a major portion of 20 to 24 carbon atoms; 0.1 to 5 percent (preferably less than 3 percent) of water soluble surfactant; and at least 70 percent (preferably greater than 75 percent, most preferably at least 77 percent) water. The dispersion is provided with a maximum particle size of 3000 Å (preferably a maximum of 1500 Å). Optionally, the solution may contain at least 0.1 percent of a wood preservative and/or 1 to 15 percent of a resin.

In the concentrate form, the compositions of the present invention may be characterized as an aqueous dispersion comprising (all percentages being on a weight basis): at least 4 percent but less than 40 percent (preferably less than 35 percent) of a porous substrate penetrating, organic solvent; at least 4 percent (preferably at least 6 percent) of a water repellent selected from the group consisting of an alpha-olefin or paraffin blend having a major portion of 20 to 24 carbon atoms; 0.5 to 20 percent (preferably 1 to 10 percent, most preferably lest than 9 percent) of water soluble surfactant; and at least 20 percent (preferably greater than 30 percent, most preferably 35 to 50 percent) water. The dispersion is provided with a maximum particle size of 3000 Å (preferably a maximum of 1500 Å). Optionally, the solution may contain at least 0.1 percent of a wood preservative and/or 1 to 15 percent of a resin.

In both the concentrate and the ready to use formulation the amount of water repellent is high relative to the amount of organic solvent, thus achieving water repellency while maintaining low V.O.C. Penetration into the porous substrate is achieved by providing small particle size of the dispersion, which in turn is achieved by mechanical means rather than relying on surfactants. The concentrate is in the form of an aqueous dispersion having the requisite particle size so that dilution to the ready to apply concentration may be carried out simply by adding water. In those embodiments containing a wood preservative, the concentration of the preservative relative to the organic solvent is also relatively high in both the concentrate and dilute forms.

Also encompassed by the invention is a method for making the dispersions and coating of this invention preferably by microfluidization. Further encompassed by the invention is a method of treating porous substrates such as wood which comprises applying the water-repellant composition of this invention to the wooden substrate followed by drying the wooden substrate. The resultant treated wooden substrate can be optionally coated or cladded. While the treatment composition is described herein with particularity to wood treating compositions, the present invention encompasses treating compositions for other porous substrates such as textiles and concrete.

DETAILED DESCRIPTION OF THE INVENTION

As set forth hereinabove, the aqueous treating composition of the invention is an oil-in-water dispersion. By the term "oil-in-water dispersion" is meant that the dispersed phase herein is an oil and the continuous phase is water or an aqueous medium.

The dispersed phase of the oil-in-water dispersion of this invention is in the range of about 5 to 80 and preferably 10 to 70 percent by weight based on total weight of the dispersion in the concentrate form. In the dilute, ready to use form, the dispersed phase may constitute about 5 to 30 percent by weight of the total dispersion. The dispersed phase comprises a solvent medium containing a mixture of solvents which are substrate-penetrating solvents, and further comprises a water repellent.

The useful wood penetrating solvents for example, are selected on the basis that they are generally non-polar and do not appreciably associate with the wood components, e.g., by hydrogen bonding. Illustrative but non-limiting examples of the solvents can be xylene, toluene, mineral spirits, naphtha, ketones, commercially available aromatic mixtures, and combinations thereof.

The water repellent of the dispersed phase comprises an alpha olefin or paraffin blend having about 20 to 24 carbon atoms or a mixture thereof with the alpha olefin blend being preferred. The individual cuts of alpha olefin having about 20 to 24 carbon atoms are useful, though such cuts are not readily available and are generally less preferred for this reason. The paraffin material can only be used as a blend of compounds as described below, it being found that individual paraffins do not provide the desired water-repellency results. The olefin and paraffin blends are characterized by consisting essentially of a narrow range of carbon compounds. That is, while paraffins are well known and have been used extensively heretofore, such materials are blends of a wide range of different carbon chain length materials. These commonly used paraffin blends are difficult to coat over and do not provide the good water-repellency efficiencies of the olefin and paraffin compounds described herein. It has been found that narrow molecular weight blends (cuts) of olefin and/or paraffin provide good water-repellency to wood. At least about 50 percent of the olefin blend or paraffin blend consists essentially of compounds having from 20 to 24 carbon atoms. Preferably, the olefin blend and paraffin blend contain at least about 70 percent and, more preferably, at least about 90 percent of the compounds having between 20 and 24 carbon atoms. The most preferred blend contains at least about 96 percent of the compounds having 20 to 24 carbon atoms and less than about 3 percent of the compounds having less than 20 carbon atoms and less than about 1 percent having more than 24 carbon atoms.

Substituted and unsubstituted hydrocarbon resins particularly alkyd resins have conventionally been used in wood-treating compositions to provide a degree of water-repellency and to aid holdout of subsequently applied materials, and such resins may optionally be included in the compositions of the present invention. Examples of alkyd resins that may be used include polyesters of polyhydroxyl alcohols and polycarboxyl acids chemically combined with various drying, semi-drying and nondrying oils in different proportions. Thus, for example, the alkyd resins are made from polycarboxylic acids such as phthalic acid, maleic acid, fumaric acid, isophthalic acid, succinic acid, adipic acid, azelaic acid, sebacic acid as well as from anhydrides of such acids where they exit. The polyhydric alcohols which are reacted with the polycarboxylic acid include glycerol, trimethylolethane, trimethylolpropane, pentaerythritol, sorbitol, mannitol, ethylene glycol, diethylene glycol and 2,3-butylene glycol. The alkyd resins are produced by reacting the polycarboxylic acid and the polyhydric alcohol together with a drying, semi-drying or non-drying oil in proportions depending upon the properties desired. The oils are coupled into the resin molecule by esterification during the manufacturing and become an integral part of the polymer. The oil is fully saturated or predominately unsaturated. The fully saturated oils tend to give a plasticizing effect to the alkyd, whereas the predominately unsaturated oils tend to crosslink and dry rapidly with oxidation to give more tough and durable alkyd resins. Suitable oils include coconut oil, fish oil, linseed oil, tung oil, castor oil, cottonseed oil, safflower oil, soybean oil and tall oil. Various proportions of the polycarboxylic acid, polyhydric alcohol and oil are used to obtain alkyd resins of various properties. Phenolic modified hydrocarbon resins such as NEVILLAC 10° XL, available from Neville Chemical Co. have also been found to be particularly useful in providing water repellency and hold out.

Many known compounds which are useful as substrate preservatives for some porous substrate such as wood. Examples of wood preservatives include carbamates such as 3-iodo-2-propynyl butyl carbamate; organic tin compounds, e.g., triphenyl and tributyl tin oxide; chlorinated compounds, e.g., tri-, tetra- and pentachlorophenol, mono- and dichloro naphthalenes, and metal naphthenates, e.g., zinc and copper naphthenates, and quaternary ammonium compounds. The preservative content can be from about 0 to 20 percent and typically 0.5 to 20 percent by weight of the dispersed phase.

Other conventional additives can be included in the treating composition of this invention. For example, surface modifiers, insecticides, biostatic agents, biocides or a mixture thereof can be employed. Pigments can also be employed herein.

In the process of this invention, the intended ingredients of the dispersion, including the optional ingredients, are dispersed in an aqueous medium with a dispersing means such as a homogenizer. Typically, a mixture of the organic component is adapted to a form that will admit it to the dispersing means. Illustratively, the organic component is in the form of a solution or is dissolved with a solvent or a mixture of solvents and then introduced into an aqueous medium in the presence of a stabilizer.

Typically, the solvent employed in the composition is selected from the aforedescribed substrate-penetrating solvents. Preferably, a cosolvent is employed as well. It is believed that the primary solvent, which is preferably a non-polar solvent, dissolves the mixture, and the cosolvent, which is preferably polar, enhances the stability of the resultant composition. The organic component dissolved in the solvent is dispersed in an aqueous medium in the presence of a stabilizer which is typically a surfactant or a combination of surfactants. The resultant mixture can be described as an emulsion.

The stabilizer can be a surfactant which is typically an anionic and/or a nonionic surfactant, preferably a combination of both, most preferably in combination with an alcohol containing about 6 to 20 carbon atoms ($C_6$–$C_{20}$ alcohol). Specific but non-limiting examples of the surfactant combinations can be found in the working examples of the invention. Amounts of about 0.5 to 20 percent, preferably 1 to 10 percent, and most preferably less than 9 percent by weight resin solids of surfactant based on the concentrate composition can be employed. In the case of the ready to use composition, the surfactants may comprise 0.1 to 5 percent, preferably at least 1 percent and less than 3 percent, of the total composition. It has been found to be advantageous for the surfactant component to comprise roughly equal portions of anionic and nonionic surfactants, with a preference for slightly more than half of the surfactant being the nonionic surfactant. Optionally, up to about 10 percent by weight (e.g., 1 to 10 percent) and preferably about 2 to 6 percent by weight $C_6$–$C_{20}$ alcohol based on the total concentrate composition can be employed. In the dilute, ready to use form, the composition may include up to 2 percent by weight (e.g., 0.2 to 2 percent), preferably about 0.5 to 1.5 percent of the alcohol. Expressed differently, it is beneficial for the alcohol to be present in amounts equal to 20 percent to 100 percent of the total weight of surfactants present. Although a small amount of the alcohol appears to enhance the stabilizing effect of the surfactants, excessive amounts of the alcohol have a detrimental effect on the ability of the compositions to penetrate wood substrates due to its polar nature. In the preferred embodiment of the invention, the surfactant combination comprises an anionic surfactant and a nonionic co-surfactant in combination with the $C_6$–$C_{20}$ alcohol. It has been found that such a surfactant combination can improve stability of the dispersions of the invention.

The emulsion can be particulated by subjecting it to stress by a homogenizing means. The mixture is subjected to stress sufficient to produce microparticles which have a mean particle size diameter of about 500 to 3,000 angstroms (Å) and typically about 500 to 1500 Å, preferably in monomodal distribution.

A preferred mode of subjecting the mixture to the appropriate stress is by the use of a MICROFLUIDIZER ® emulsifier, which is available from Microfluidics Corporation in Newton, Mass. The MICROFLUIDIZER ® high-pressure impingement emulsifier is patented in U.S. Pat. No. 4,533,254, which is incorporated herein by reference. The device consists of a high pressure (up to 20,000 pounds per square inch "psi") pump and an interaction chamber wherein the emulsification takes place. The pump forces the mixture of ingredients in an aqueous medium into the chamber where it is split into at least two streams which pass at very high velocity through at least two splits and collide resulting in the particulation of the mixture into small particles. Generally, the mixture is passed through the emulsifier once at a pressure between 5,000 and 15,000 psi. Multiple passes can result in smaller average particle size and a narrower range for the particle size distribution. When using the aforesaid MICROFLUIDIZER ® emulsifier, stress is applied by liquid impingement as has been described. However, it should be understood that, if desired, other modes of applying stress to the pre-emulsification mixture can be utilized so long as sufficient stress is applied to achieve the requisite particle size distribution, that is, such that, less than 20 percent of the resultant microparticles have a mean diameter greater than 5 microns in the resultant product. Alternate means of applying stress, e.g., the use of ultrasonic energy can be employed.

Stress is described as a force per unit area. Although the precise mechanism by which the MICROFLUIDIZER ® emulsifier stresses the pre-emulsification mixture to particulate is not thoroughly understood, it is theorized that stress is exerted in more than one manner. It is believed that one manner in which stress is exerted is by shear. "Shear" means that the force is such that one layer or plane moves parallel to an adjacent parallel plane. Stress can also be exerted from all sides as a bulk compression stress. In this instance, stress could be exerted without any shear. A further manner of producing intense stress is by cavitation. Cavitation occurs when the pressure within a liquid is reduced enough to cause vaporization. The formation and collapse of the vapor bubbles occurs violently over a short time period and produces intense stress. Although not intending to be bound by theory, it is believed that both shear and cavitation contribute to producing the stress which particulates the mixture.

The resultant dispersion can be in the form of a concentrate containing from about 5 to 80 percent and preferably from about 10 to 70 percent dispersed organic phase based on the total weight at ambient temperature. In other words, the dispersed concentrate contains at least 20 percent by weight, preferably at least 30 percent, and most preferably at least 35 percent, water. Preferably the amount of water in the concentrate is minimized to that required to produce a stable external aqueous phase. In the examples of particular compositions disclosed herein the amount of water required to produce a stable dispersion did not exceed 50 percent by weight of the dispersion, but larger amounts of water may be included in the concentrate if desired, limited only by the general desirability to minimized the volume and weight of the concentrate for shipping and handling. The concentrate is generally further diluted by mixing with water to form a ready-to-use dispersion. Typically the dilution is at a ratio of three parts by volume water to one part by volume of the concentrate, and in preferred embodiments the ratio may be about four parts water to one part of the concentrate. Since the concentrate is already a dispersion, the dilution need only involve simple stirring or the like.

Compositions of this invention comprising the dispersion are especially useful when used for treating wood. The compositions can be applied by any conventional method including dipping, flow coating, roll coating, and in a vacuum/pressure apparatus. Generally, the amount of treating composition applied is sufficient to provide the wood with the desired water-repellency. Water repellency of the treated composition can be at a level of at least 40 percent and preferably 50 percent and more preferably 60 percent as determined by NWMA-M-2-81 Swellometer test with an immersion time of 30 seconds. The wood, after being treated, is optionally further processed and then dried.

Further illustrating the invention are the following non-limiting examples.

EXAMPLE 1

The following treatment composition of this invention was formulated as follows. In a 1 liter beaker was placed 8.1 percent $C_{20}$-$C_{24}$ alpha olefin[1], 13.4 percent hydrocarbon resin[2], 2.0 percent 3-iodo-2-propynyl butyl carbamate[3], 4.1 percent anionic[4] and 6.1 percent nonionic[5] surfactants, 4.1 percent alcohol[6], 0.284 percent microbiocide[7], and finally 20.4 percent "Solvesso 150"[8]. The mixture was warmed until all the components formed a homogeneous liquid. The liquid was then introduced into a dispersing apparatus[9] and water was added until there was a drastic increase in viscosity (the solution had a viscosity in excess of 200 centipoises (cps) at this point, which was its inversion point). The resultant emulsion was a concentrate in the form of an oil-in-water emulsion that could be further diluted with water.

(1) Available from Chevron Chemical as a "$C_{20}$-$C_{24}$ alpha olefin".
(2) Available from Neville Chemical as "Nevillac 10° XL".
(3) Available from Troy Chemical as "Polyphase P-100".
(4) Available from GAF Corporation as "Alipal CO-436".
(5) Available from GAF Corporation as "Igepal CO-897".
(6) Available from Exxon as "Exxal 13".
(7) Available from ICI Americas as "Proxel CRL".
(8) Available from Exxon as "Solvesso 150".
(9) Available from Microfluidics Corporation as "Microfluidizer ® emulsifier".

EXAMPLE 2

The emulsion from Example 1 was diluted by three parts by volume water to one part by volume concentrate to yield a ready-to-use wood-treating composition. The water repellency of the composition was tested following the NWMA #M-2-81 test method. The wood preservative properties were tested by NWMA Soil Block Test #M-1-81 at Mississippi State University. The ready to use wood treating composition was as follows:

| Ingredient | Percent Compositions |
| --- | --- |
| Alpha Olefin[1] | 2.0 |
| Hydrocarbon Resin[2] | 3.3 |
| Preservative[3] | .50 |
| Solvent[4] | 5.0 |
| Surfactant 1[5] | 1.0 |
| Surfactant 2[6] | 1.5 |
| Alcohol[7] | 1.0 |
| Microbiocide[8] | .07 |
| Water | 85.63 |

[1] Available from Chevron Chemical as a "$C_{20}$-$C_{24}$ alphpa olefin".
[2] Available from Neville Chemical as "Nevillac 10° XL".
[3] Available from Troy Chemical as "Polyphase P-100".
[4] Available from Exxon as "Solvesso 150".
[5] Available from GAF Corporation as "Alipal CO-436".
[6] Available from GAF Corporation as "Igepal CO-897".
[7] Available from Exxon as "Exxal 13".
[8] Available from ICI Americas as "Proxel CRL".

Three to five matched wood wafers were dipped in the above composition for a period of 30 seconds as prescribed by the NWMA M-2-81 Swell-O-Meter test procedure. A water-repellency efficiency of 70.1 after five days was obtained.

The above composition was sent to Mississippi State University for soil block testing. Summary of the individual percent weight losses of treated southern yellow pine blocks ($3.05 \times 19 \times 19$ mm) after exposure to brown-rot fungus (*G. trabeum*) for five weeks are stated in the table below.

TABLE 1

| FORMULA | % CONCEN-TRATION | BLOCK # | RETENTION (pcf)[1] BIOCIDE | W1[2] (g) | W2[3] (g) | % WT. LOSS | VISUAL INSPECT. |
| --- | --- | --- | --- | --- | --- | --- | --- |
| Ex. 1 | 100.00% | W-21 | 54.430 | 1.04 | 1.04 | 0.000 | ND[4] |
| | | W-22 | 51.028 | 1.10 | 1.10 | 0.000 | ND |
| | | W-23 | 53.863 | 1.10 | 1.10 | 0.000 | ND |
| | | W-24 | 67.470 | 0.93 | 0.91 | 2.150 | ND |
| | | W-25 | 69.171 | 0.94 | 0.93 | 1.060 | ND |
| Control | — | W-31 | 0.000 | 0.97 | 0.51 | 47.42 | D[5] |
| | | W-32 | 0.000 | 0.93 | 0.54 | 41.94 | D |
| | | W-33 | 0.000 | 0.95 | 0.46 | 51.58 | D |
| | | W-34 | 0.000 | 0.80 | 0.39 | 51.25 | D |
| | | W-35 | 0.000 | 0.77 | 0.45 | 41.56 | D |

[1] pcf stands for pounds per cubic foot.
[2] W1 stands for initial weight in grams (g) of the wood before exposure to the fungus.
[3] W2 stands for weight in grams (g) of the wood after exposure to the fungus.
[4] ND stands for "No Decay" upon visual inspection.
[5] D stands for "Decay" upon visual inspection.

EXAMPLE 3

The following shows the effects of various resins on the water repellency efficiency of the treatment composition. The treatment composition was essentially the same as in Example 1 except that different hydrocarbon resins were employed and the concentrate was diluted to yield the following compositions.

| Composition (%) | A | B | C |
| --- | --- | --- | --- |
| Alpha Olefin[1] | 2.0 | 2.6 | 5.0 |
| Hydrocarbon Resin[2] | 3.3 | | |
| Hydrocarbon Resin[3] | | 14.1 | |
| Hydrocarbon Resin[4] | | | 11.6 |
| Preservative[5] | .50 | .50 | .50 |
| Solvent[6] | 5.0 | 5.0 | 5.0 |
| Surfactant 1[7] | 1.0 | .50 | |
| Surfactant 2[8] | 1.0 | | .50 |
| Alcohol[9] | 1.5 | .20 | 1.5 |
| Microbiocide[10] | .07 | .07 | .07 |
| Water | 85.63 | 77.03 | 81.33 |

-continued

| Composition (%) | A | B | C |
|---|---|---|---|
| Water-repellency | 70.1 | 55.3 | 64.3 |

[1]Available from Chevron Chemical as a "$C_{20}$-$C_{24}$ alpha olefin".
[2]Available from Neville Chemical as "Nevillac 10° XL".
[3]A dehydrated castor oil short oil alkyd.
[4]A soya oil long oil alkyd.
[5]Available from Troy Chemical as "Polyphase P-100".
[6]Available from Exxon as "Solvesso 150".
[7]Available from GAF Corporation as "Alipal CO-436".
[8]Available from GAF Corporation as "Igepal CO-897".
[9]Available from Exxon as "Exxal 13".
[10]Available from ICI Americas as "Proxel CRL".

EXAMPLE 4

This example shows the importance of the alpha olefin as compared to paraffin wax for water-repellency efficiency. The following formulations were made and tested for water repellency as described in Example 2:

| Composition | Water-repellency |
|---|---|
| Example 1 | 70.1 |
| Example 1 (with paraffin[1] instead of alpha olefin) | 14.8 |

[1]From W&F Manufacturing Corporation, Buffalo, New York.

EXAMPLE 5

This example illustrates the efficiency of the treatment with respect to dip time. The composition of Example 1 was formulated and the same procedure was followed for reduction. The water-repellency efficiency measurement was conducted as per NWMA M-81 test except that the employed wafers were dipped for 20 and 30 seconds. The results after 5 days were:

| Composition | Dip Time | Water-repellency |
|---|---|---|
| Example 1 | 20 sec. | 60.1 |
| Example 1 | 30 sec. | 70.1 |
| "Woodlife Milltreat F[1]" | 30 sec. | 75.8 |

[1]A solvent based water repellent wood preservative product available from Beecham Home Improvement Products, Inc.

The results clearly show that even using a short dip time of the water-base material, the water repellency efficiency is good. Also, the data shows that this formulation is comparable in efficiency to a commercially available solvent based, water repellent, preservative solution, "Woodlife Milltreat F."

EXAMPLE 6

This experimental design used to determine the optimal surfactant levels illustrates the interaction between the surfactant levels and penetration of the preservative. The compositions were formulated as in Example 1 indicated and diluted as in Example 2 to yield the following compositions.

| Ingredient | Percent Composition | | | | | | | |
|---|---|---|---|---|---|---|---|---|
|  | A | B | C | D | E | F | G | H |
| Alpha Olefin[1] | 2.0 | 2.0 | 2.0 | 2.0 | 2.0 | 2.0 | 2.0 | 2.0 |
| Hydrocarbon Res.[2] | 3.3 | 3.3 | 3.3 | 3.3 | 3.3 | 3.3 | 3.3 | 3.3 |
| Preservative[3] | .50 | .50 | .50 | .50 | .50 | .50 | .50 | .50 |
| Solvent[4] | 5.0 | 5.0 | 5.0 | 5.0 | 5.0 | 5.0 | 5.0 | 5.0 |
| Alcohol[5] | 1.0 | 1.0 | 1.0 | 1.0 | 2.0 | 2.0 | 2.0 | 2.0 |
| Surfactant 1[6] | 1.0 | .50 | 1.0 | .50 | 1.0 | .50 | 1.0 | .50 |
| Surfactant 2[7] | .80 | .80 | 1.5 | 1.5 | 1.5 | 1.5 | .80 | .80 |
| Microbiocide[8] | .07 | .07 | .07 | .07 | .07 | .07 | .70 | .70 |
| Water | 86.33 | 86.83 | 85.63 | 86.13 | 84.63 | 85.13 | 85.33 | 85.83 |

[1]Available from Chevron Chemical as a "$C_{20}$-$C_{24}$ alpha olefin".
[2]Available from Neville Chemical as "Nevillac 10° XL".
[3]Available from Troy Chemical as "Polyphase P-100".
[4]Available from Exxon as "Solvesso 150".
[5]Available from Exxon as "Exxal 13".
[6]Available from GAF Corporation as "Alipal CO-436".
[7]Available from GAF Corporation as "Igepal CO-897".
[8]Available from ICI Americas as "Proxel CRL".

After a 30 second dip in the treatment, the 1.125×1.125×12.0 inch pine penetration blocks were allowed to dry for seven days at room temperature. The blocks were then planed on all four faces until they measure 1.0×1.0×12.0 inch and then cut into 0.25 inch thick wafers and crushed for detection of the active ingredient by "Soxhlet" extraction.

| Solution | Depth into wood (inches) | Penetration of IPBC |
|---|---|---|
| A | .25 | .765 ug |
|  | .50 | <.02 ug |
| B | .25 | .681 ug |
|  | .50 | <.02 ug |
| C | .25 | .682 ug |
|  | .50 | .841 ug |
|  | .75 | .634 ug |
|  | 1.00 | 1250 ug |
|  | 1.25 | 983 ug |
|  | 1.50 | 880 ug |
|  | 1.75 | 1030 ug |
|  | 2.00 | 460 ug |
| D | .25 | .538 ug |
|  | .50 | .023 ug |
| E | .25 | .590 ug |
|  | .50 | <.020 ug |
| F | .25 | .612 ug |
|  | .50 | <.020 ug |
| G | .25 | .659 ug |
|  | .50 | <.020 ug |
| H | .25 | .672 ug |
|  | .50 | <.020 ug |

The results show that the levels of the various surfactants chosen in sample "C" optimize the penetration of the preservative to a depth far beyond the others.

EXAMPLE 7

This example shows the versatility of the formulation which allows one to change the active ingredient to fit the product requirements. The following emulsions were formulated as in Example 1 and diluted as in Example 2 to yield the following:

| Ingredient | Percent Composition | | |
|---|---|---|---|
|  | A | B | C |
| Alpha Olefin[1] | 2.0 | 2.0 | 2.0 |
| Hydrocarbon Resin[2] | 3.3 | 3.3 | 3.3 |
| Preservative[3] | .50 |  |  |
| Preservative[4] |  | 1.0 |  |
| Preservative[5] |  |  | 3.0 |
| Solvent[6] | 5.0 | 5.0 | 5.0 |
| Surfactant 1[7] | 1.0 | 1.0 | 1.0 |
| Surfactant 2[8] | 1.0 | 1.0 | 1.0 |
| Alcohol[9] | 1.5 | 1.5 | 1.5 |
| Microbiocide[10] | .07 | .07 | .07 |
| Water | 85.63 | 85.13 | 83.13 |

The products were stable for at least three months in

-continued

| Ingredient | Percent Composition | | |
|---|---|---|---|
| | A | B | C |
| ambient temperatures and in a 120° hot room. | | | |

[1]Available from Chevron Chemical as a "$C_{20}$-$C_{24}$ alpha olefin".
[2]Available from Neville Chemical as "Nevillac 10° XL".
[3]Available from Troy Chemical as "Polyphase P-100".
[4]Available from Beckman Laboratories as "Busan 1009".
[5]Available from Sherex Chemicals as "Adogen 432".
[6]Available from Exxon as "Solvesso 150".
[7]Available from GAF Corporation as "Alipal CO-436".
[8]Available from GAF Corporation as "Igepal CO-897".
[9]Available from Exxon as "Exxal 13".
[10]Available from ICI Americas as "Proxel CRL".

EXAMPLE 8

This illustration shows the versatility of the formulation which allows one to change the solvent system to fit the product application. The following formulations were formulated as stable samples as in Example 1 and diluted as in Example 2 to yield the following formulations:

| Ingredient | Percent Composition | | | | | |
|---|---|---|---|---|---|---|
| | A | B | D | E | F | G |
| Alpha Olefin[1] | 2.0 | 2.0 | 2.0 | 2.0 | 2.0 | 2.0 |
| Hydrocarbon Resin[2] | 3.3 | 3.3 | 3.3 | 3.3 | 3.3 | 3.3 |
| Preservative[3] | .50 | .50 | .50 | .50 | .50 | .50 |
| Solvent[4] | 5.0 | | | | | |
| Solvent[5] | | 5.0 | | | | |
| Solvent[6] | | | 5.0 | | | |
| Solvent[7] | | | | 5.0 | | |
| Solvent[8] | | | | | 5.0 | |
| Solvent[9] | | | | | | 5.0 |
| Alcohol[10] | 1.0 | 1.0 | 1.0 | 1.0 | 1.0 | 1.0 |
| Surfactant 1[11] | 1.0 | 1.0 | 1.0 | 1.0 | 1.0 | 1.0 |
| Surfactant 2[12] | 1.5 | 1.5 | 1.5 | 1.5 | 1.5 | 1.5 |
| Microbiocide[13] | .07 | .07 | .07 | .07 | .07 | .70 |
| Water | 85.63 | 85.63 | 85.63 | 85.63 | 85.63 | 85.63 |

[1]Available from Chevron Chemical as a "$C_{20}$-$C_{24}$ alpha olefin".
[2]Available from Neville Chemical as "Nevillac 10° XL".
[3]Available from Troy Chemical as "Polyphase P-100".
[4]Available from Exxon as "Solvesso 150".
[5]Xylene available from Ashland Chemical.
[6]Methyl isobutyl ketone available from Exxon.
[7]Cyclohexanone available from Ashland Chemical.
[8]Odorless kerosene available from Aldrich.
[9]Mineral spirits available from Ashland Chemical.
[10]Available from Exxon as "Exxal 13".
[11]Available from GAF Corpration as "Alipal CO-436".
[12]Available from GAF Corporation as "IgePal CO-897".
[13]Available from ICI Americas as "Proxel CRL".

As aforestated, the invention in its broad embodiment encompasses a water-repellant composition for porous substrates other than wood. While the illustrative embodiments of the invention have been described hereinabove with particularity, it will be understood that various modifications of the invention will be apparent to those skilled in the art without departing from the scope or spirit of the invention. Accordingly, the claims directed to the invention are intended to be construed as encompassing all aspects of the invention which would be treated as equivalents by one skilled in the art to which the invention pertains.

What is claimed is:

1. An aqueous composition for treating a porous substrate in the form of an oil-in-water dispersion comprising (on a weight basis):
   at least 1 percent but less than 10 percent of a porous substrate penetrating, organic solvent;
   at least 1 percent of a water repellent substance at least 50 percent of which comprises a compound or compounds having 20 to 24 carbon atoms and selected from the group consisting of alpha-olefins and paraffin blends;
   0.1 to 5 percent of water soluble surfactant;
   0.2 to 2 percent of an alcohol having 6 to 20 carbon atoms; and
   at least 70 percent water;
   the dispersed phase characterized by mean particle size of no more than 3000 Å.

2. The aqueous dispersion of claim 1 wherein the organic solvent is present in the amount of 1 to 7.5 percent.

3. The aqueous dispersion of claim 1 wherein the dispersed phase has a mean particle size of no more than 1500 Å.

4. The aqueous dispersion of claim 1 wherein the surfactant is present in an amount less than 3.0 percent.

5. The aqueous dispersion of claim 4 wherein the surfactant is present in an amount of at least one percent.

6. The aqueous dispersion of claim 1 wherein the surfactant includes an anionic surfactant and a nonionic surfactant.

7. The aqueous dispersion of claim 1 wherein the water repellent is present in an amount of at least 1.5 percent.

8. The aqueous dispersion of claim 1 wherein the water is present in an amount greater than 75 percent.

9. The aqueous dispersion of claim 1 wherein the water is present in an amount of at least 77 percent.

10. The aqueous dispersion of claim 1 further including 1 to 15 percent of a resin.

11. The aqueous dispersion of claim 1 further including 0.1 to 20 percent of a biocidal preservative.

12. The aqueous dispersion of claim 1 wherein the volatile organic content is less than 3.5.

13. The aqueous dispersion of claim 1 wherein the volatile organic content is less than 3.0.

14. The aqueous dispersion of claim 1 wherein the alcohol having 6 to 20 carbon atoms is present in an amount equal to 20 percent to 100 percent of the weight of surfactants present.

15. A water reducible concentrate composition for treating a porous substrate in the form of an oil-in-water dispersion comprising (on a weight basis):
   at least 4 percent but less than 40 percent of a porous substrate penetrating, organic solvent;
   at least 4 percent of a water repellent substance at least 50 percent of which comprises a compound or compounds having 20 to 24 carbon atoms and selected from the group consisting of alpha-olefins and paraffin blends;
   0.5 to 20 percent of water soluble surfactant;
   0.5 to 8 percent of an alcohol having 6 to 20 carbon atoms; and
   at least 20 percent water;
   the dispersed phase characterized by mean particle size of no more than 3000 Å.

16. The concentrate dispersion of claim 15 wherein the organic solvent is present in an amount of at least 10 percent and less than 35 percent.

17. The concentrate dispersion of claim 16 wherein the organic solvent is present in an amount less than 30 percent.

18. The concentrate dispersion of claim 15 wherein the dispersed phase has a mean particle size of no more than 1500 Å.

19. The concentrate dispersion of claim 15 wherein the surfactant is present in an amount of 1 to 10 percent.

20. The concentrate dispersion of claim 19 wherein the surfactant is present in an amount less than 9 percent.

21. The concentrate dispersion of claim 15 wherein the surfactant includes an anionic surfactant and a nonionic surfactant.

22. The concentrate dispersion of claim 15 wherein the water repellent is present in an amount of at least 6 percent.

23. The concentrate dispersion of claim 15 wherein the water is present in an amount greater than 30 percent.

24. The concentrate dispersion of claim 15 wherein the water is present in an amount of 35 to 50 percent.

25. The concentrate dispersion of claim 15 further including 1 to 60 percent of a resin.

26. The concentrate dispersion of claim 15 further including 0.5 to 20 percent of a biocidal preservative.

27. The concentrate dispersion of claim 15 wherein the alcohol having 6 to 20 carbon atoms is present in an amount equal to 20 percent to 100 percent of the weight of surfactants present.

28. A water reducible concentrate composition for treating a porous substrate in the form of an oil-in-water dispersion comprising (on a weight basis):
   at least 4 percent but less than 40 percent of a porous substrate penetrating, organic solvent;
   at least 6 percent of a water repellent substance at least 50 percent of which comprises a compound or compounds having 20 to 24 carbon atoms and selected from the group consisting of alpha-olefins and paraffin blends;
   0.5 to 20 percent of water soluble surfactant; and
   at least 20 percent water;
the dispersed phase characterized by mean particle size of no more than 3000 Å.

* * * * *